US008404653B2

(12) United States Patent
Zsebo

(10) Patent No.: US 8,404,653 B2
(45) Date of Patent: Mar. 26, 2013

(54) MEMBRANE BOUND STEM CELL FACTOR THERAPY FOR ISCHEMIC HEART

(75) Inventor: Krisztina M. Zsebo, Del Mar, CA (US)

(73) Assignee: Enterprise Partners Venture Capital, La Jolla, CA (US)

(*) Notice: Subject to any disclaimer, the term of this patent is extended or adjusted under 35 U.S.C. 154(b) by 879 days.

(21) Appl. No.: 12/084,673

(22) PCT Filed: Nov. 13, 2006

(86) PCT No.: PCT/US2006/043937
§ 371 (c)(1),
(2), (4) Date: Jul. 28, 2009

(87) PCT Pub. No.: WO2007/059010
PCT Pub. Date: May 24, 2007

(65) Prior Publication Data
US 2009/0304636 A1 Dec. 10, 2009

Related U.S. Application Data

(60) Provisional application No. 60/737,058, filed on Nov. 14, 2005.

(51) Int. Cl.
*A61K 48/00* (2006.01)
*A01N 63/00* (2006.01)

(52) U.S. Cl. ............ 514/44 R; 424/93.2; 536/23.1

(58) Field of Classification Search .............. None
See application file for complete search history.

(56) References Cited

U.S. PATENT DOCUMENTS

| 3,760,984 | A | 9/1973 | Theeuwes |
| 3,845,770 | A | 11/1974 | Theeuwes et al. |
| 3,916,899 | A | 11/1975 | Theeuwes et al. |
| 3,923,426 | A | 12/1975 | Theeuwes |
| 3,987,790 | A | 10/1976 | Eckenhoff et al. |
| 3,995,631 | A | 12/1976 | Higuchi et al. |
| 4,016,880 | A | 4/1977 | Theeuwes et al. |
| 4,036,228 | A | 7/1977 | Theeuwes |
| 4,111,202 | A | 9/1978 | Theeuwes |
| 4,111,203 | A | 9/1978 | Theeuwes |
| 4,203,440 | A | 5/1980 | Theeuwes |
| 4,203,442 | A | 5/1980 | Michaels |
| 4,210,139 | A | 7/1980 | Higuchi |
| 4,327,725 | A | 5/1982 | Cortese et al. |
| 4,360,019 | A | 11/1982 | Portner et al. |
| 4,487,603 | A | 12/1984 | Harris |
| 4,627,850 | A | 12/1986 | Deters et al. |
| 4,692,147 | A | 9/1987 | Duggan |
| 4,725,852 | A | 2/1988 | Gamblin et al. |
| 4,865,845 | A | 9/1989 | Eckenhoff et al. |
| 5,057,318 | A | 10/1991 | Magruder et al. |
| 5,059,423 | A | 10/1991 | Magruder et al. |
| 5,112,614 | A | 5/1992 | Magruder et al. |
| 5,137,727 | A | 8/1992 | Eckenhoff |
| 5,234,692 | A | 8/1993 | Magruder et al. |
| 5,234,693 | A | 8/1993 | Magruder et al. |
| 5,387,419 | A | 2/1995 | Levy et al. |
| 5,437,994 | A | 8/1995 | Emerson et al. |
| 5,634,895 | A | 6/1997 | Igo et al. |
| 5,646,043 | A | 7/1997 | Emerson et al. |
| 5,670,147 | A | 9/1997 | Emerson et al. |
| 5,670,351 | A | 9/1997 | Emerson et al. |
| 5,681,278 | A | 10/1997 | Igo et al. |
| 5,728,396 | A | 3/1998 | Peery et al. |
| 5,797,870 | A | 8/1998 | March et al. |
| 5,827,216 | A | 10/1998 | Igo et al. |
| 5,900,433 | A | 5/1999 | Igo et al. |
| 5,931,810 | A | 8/1999 | Grabek |
| 5,935,565 | A | 8/1999 | Besmer et al. |
| 5,985,305 | A | 11/1999 | Peery et al. |
| 6,080,728 | A | 6/2000 | Mixson |
| 6,093,531 | A | 7/2000 | Bjornson et al. |
| 6,207,417 | B1 | 3/2001 | Zsebo et al. |
| 6,218,148 | B1 | 4/2001 | Zsebo et al. |
| 6,251,418 | B1 | 6/2001 | Ahern et al. |
| 6,258,119 | B1 | 7/2001 | Hussein et al. |
| 6,261,549 | B1 | 7/2001 | Fernández et al. |
| 6,326,198 | B1 | 12/2001 | Emerson et al. |
| 6,723,561 | B2 | 4/2004 | Russell et al. |
| 6,759,215 | B1 | 7/2004 | Zsebo et al. |
| 7,078,387 | B1* | 7/2006 | Leiden et al. ............ 514/44 R |
| 7,285,540 | B2* | 10/2007 | Morishita et al. ......... 514/44 R |
| 2002/0010462 | A1 | 1/2002 | Altman |

(Continued)

FOREIGN PATENT DOCUMENTS

| CA | 2 213 906 | 3/1998 |
| WO | WO 97/16170 | 5/1997 |

(Continued)

OTHER PUBLICATIONS

Alberts et al., Chapter 12: Intracellular Compartments and Protein Sorting, Molecular Biology of the Cell, 3$^{rd}$ Ed., New York, NY Garland Publishing 551-598 (1994).
Anderson, W.F., Human Gene Therapy, Science, 256(5058):808-813 (1992).
Andrews et al., Tumor Necrosis Factor-α (TNF α) Suppression of c-kit Ligand (KL) Is Mediated by Phospholipid (PL) Intermediates in Marrow Stromal Cells (MSC), Blood 80:365A (1992).
Ayach et al., "c-Kit$^+$ BM Cells Are Essential for Reducing Deteriorating Myocardial and Heart Function Post-Myocardial Infarction" Am. Heart Assoc. Scientific Sessions 2004, Circulation Oct. 26, 2004;110(17 Suppl) abstract No. 317 (2004).
Bosse et al., Production of stem-cell transplants according to good manufacturing practice, Ann Hematol 79:469-476 (2005).
Caplen et al., Liposome-mediated *CFTR* gene transfer to the nasal epithelium of patients with cystic fibrosis, Nature Med., 1:39-46 (1995).
Cottler-Fox et. al., Stem Cell Mobilization, Am. Soc. Hematol. Educ. Program Book San Diego, Calif, pp. 419-437 (2003).
Davani et. al., Can stem cells mend a broken heart? Cardiovascular Res. 65(2):305-316 (2005).

(Continued)

*Primary Examiner* — Robert M Kelly
(74) *Attorney, Agent, or Firm* — Sheppard Mullin Richter & Hampton LLP; Anthony C. Kuhlmann

(57) ABSTRACT

The present invention relates to the use of stem cell factor (SCF) for the treatment of ischemic injured tissue such as in cardiovascular disease. The method involves administration of a nucleic acid encoding SCF, wherein the nucleic acid is delivered to the site of the injury and is incorporated into cells which then express the SCF.

8 Claims, 2 Drawing Sheets

U.S. PATENT DOCUMENTS

| | | | |
|---|---|---|---|
| 2003/0009145 | A1 | 1/2003 | Struijker-Boudier et al. |
| 2005/0222022 | A1 | 10/2005 | Greenberg et al. |
| 2006/0008450 | A1 | 1/2006 | Verfaillie et al. |

FOREIGN PATENT DOCUMENTS

| | | |
|---|---|---|
| WO | WO 97/27840 | 8/1997 |
| WO | WO 02/30443 | 4/2002 |
| WO | WO 0230443 A2 * | 4/2002 |
| WO | WO 03/069310 | 8/2003 |
| WO | WO 2005/017165 | 2/2005 |
| WO | WO 2005/053729 | 6/2005 |
| WO | WO 2005/082440 A1 | 9/2005 |
| WO | WO 2006/055260 | 5/2006 |

OTHER PUBLICATIONS

Dzau et al., Gene therapy for cardiovascular disease, *Trends in Biotechnology* 11(5):205-10 (1993).

Eck and Wilson, Gene-Based Therapy, Chapter 5 in Goodman and Gilman's *The Pharmacological Basis of Therapeutics* Ninth edition, New York:, NY, McGraw-Hill, p. 77-101 (1996).

Fazel et al., Cell transplantation preserves cardiac function after infarction by infarct stabilization: Augmentation by stem cell factor, J Thorac Cardiovasc Surg. 130(5):1310 (2005).

Fazel et. al. "Stem cell factor receptor and cardiac regeneration after myocardial infarction" Am. Heart Assoc. Scientific Sessions 2004, Circulation Oct. 24, 2004;110 (17 Suppl) abstract No. 2182. (2004).

Feugier et al., Cutting Edge Communication. Ex vivo Expansion of Stem and Progenitor Cells in Co-culture of Mobilized Perhipheral Blood CD34+ Cells on Human Endothelium Transfected with Adenovectors Expressing Thrompopoietin, c-kit Ligand, and Flt-3 Ligand, J. Hematotherapy and Stem Cell Res. 11:127-138 (2002).

Frangogiannis et al., Stem Cell Factor Induction Is Associated With Mast Cell Accumulation After Canine Myocardial Ischemia and Reperfusion, Circulation 98:687 (1998).

Gnecchi et al., Paracrine action accounts for marked protection of ischemic heart by Akt-modified mesenchymal stem cells, Nat. Med. 11:367-368 (2005).

Haider et al., Bone marrow cell transplantation in clinical perspective, J. Mol. Cell. Cardiol. 38(2):225 (2005).

Heissig et al., Low-dose irradiation promotes tissue revascularization through VEGF release from mast cells and MMP-9-mediated progenitor cell mobilization, J. Exp. Med. 202(6):739-50 (2005).

Itescu, S., Schuster, M.D., and Kocher, A.A., New directions in strategies using cell therapy for heart disease, J. Mol. Med. 81 (5):288-296 (2003).

Koyanagi et al., Cell-to-Cell Connection of Endothelial Progenitor Cells With Cardiac Myocytes by Nanotubes: A Novel Mechanism for Cell Fate Changes? Circulation Res. 96:1039-1041 (2005).

Kusano et al., Sonic hedgehog myocardial gene therapy: tissue repair through transient reconstitution of embryonic signaling, Nat Med. 11(11):1197-204 (2005).

Langley et al., Soluble stem cell factor in human serum, Blood, 81:656-660 (1993).

Lesson-Wood et al., Systemic Gene Therapy with p53 Reduces Growth and Metastases of a Malignant Human Breast Cancer in Nude Mice, *Human Gene Therapy*, 6:395-405 (1995).

Martin, F.H. et.al., Primary Structure and Functional Expression of Rat and Human Stem Cell Factor DNAs. Cell 63:203-211 (1990).

Menasché et al., Autologous Skeletal Myoblast Transplanation for Severe Postinfarction Left Ventricular Dysfunction, J. Am. Coll. Cardiol. 41(7):1078-1083 (2003).

Moore et al., Mobilization of Endothelial and Hematopoietic Stem and Progenitor Cells by Adenovector-Mediated Elevation of Serum Levels of SDF-1, VEGF, and Angiopoietin-1, Ann N Y Acad Sci. 938:36-45-47 (2001).

Nabel et at, Recombinant Gene Expression in vivo within Endothelial Cells of the Arterial Wall, Science, 244:1342-1344 (1989).

Ohtsuka et al., Cytokine therapy prevents left ventricular remodeling and dysfunction after myocardial infarction through neovascularization, The FASEB J. 18(7):851-3 (2004).

Orlic et al., Mobilized bone marrow cells repair the infarcted heart, improving function and survival, Proc. Natl. Acad. Sci (USA) 98(18):10344-10349 (2001).

Perin et. al., Transendocardial, Autologous Bone Marrow Cell Transplantation for Severe, Chronic Ischemic Heart Failure, Circulation 107:r75—r83 (2003).

Przybylska et al., Partial correction of the α-galactosidase A deficiency and reduction of glycolipid storage in Fabry mice using synthetic vectors, J. Gene Med., 6: 85-92 (2004).

Rafii et al., Efficient mobilization and recruitment of marrow-derived endothelial and hematopoietic stem cells by adenoviral vectors expressing angiogenic factors, Gene Therapy 9:631-641 (2002).

Romano et al., Latest Developments in Gene Transfer Technology: Achievements, Perspectives, and Controversies over Therapeutic Applications, *Stem Cells*, 18:19-39 (2000).

Rosenberg et al., Grafting Genetically Modified Cells to the Damaged Brain: Restorative Effects of NGF Expression, *Science*, 242:1575-1578 (1988).

Spangrude et al., Purification and Charactedrization of Mouse Hematopoietic Stem Cells, Science 241: 58-62 (1988).

Svahn et al., Adding functional entities to plasmids, J. Gene Med., 6: S36-S44 (2004).

Takada, A. and Kawaoka, Y., Antibody-dependent enhancement of viral infection: molecular mechanisms and in vivo implications, Rev. Med. Virol. 13:387-398 (2003).

Takagi et al., Cell Processing Engineering for Ex-Vivo Expansion of Hematopoietic Cells, J. Biosci Bioengineer. 99:189-196 (2005).

Takano et al., Pleiotropic Effects of Cytokines on Acute Myocardial Infarction: G-CSF as a Novel Therapy for Acute Myocardial Infarction, Current Pharmaceutical Design 9:1121-1127 (2003).

Thompson et. al., Intracardiac Transplantation of a Mixed Population of Bone Marrow Cells Improves Both Regional Systolic Contractility and Diastolic Relaxation, J. Heart Lung Transplant. 24(2):205I (2005).

Wagner et al., Transferrin-polycation conjugates as carriers for DNA uptake into cells, *Proc. Natl. Acad. Sci. USA* 87(9):3410-4 (1990).

Wilson, J.M., Vectors—shuttle vehicles for gene therapy, *Clin. Exp. Immunol.* 107 (Supp). 1):31-32 (1997).

Wives et al., Methods of Gene Delivery, *Hematology/OncologyClinics of North America, Gene Therapy*, S.L. Eck, ed., W.B. Saunders Company, Philadelphia, PA,12(3):483-501 (1998).

Woldbaek, et.al., Gene expression of colony-stimulating factors and stem cell factor after myocardial infarction in the mouse, Acta Physiol Scand 175:173-181 (2002).

Wolff et al., Grafting fibroblasts genetically modified to produce L-dopa in a rat model of Parkinson disease, *Proc. Natl. Acad. Sci. USA* 86:9011-9014 (1989).

Wolff et al., Long-term persistence of plasmid DNA and foreign gene expression in mouse muscle, Human Mol. Genet., 1:363-369 (1992).

Wolff et al., Direct Gene Transfer into Mouse Muscle in Vivo, Science, 247, 1465-1468 (1990).

Wu, G.Y. And Wu, C.H., Receptor-mediated in Vitro Gene Transformation by a Soluble DNA Carrier System, *J. Biol. Chem.* 262(10):4429-32 (1987).

Xu et al., Gene Therapy with P53 and a Fragment of Thrombospondin I Inhibits Human Breast Cancer in Vivo, *Molecular Genetics and Metabolism*, 63:103-109 (1998).

Yoon et. al., Clonally expanded novel multipotent stem cells from human bone marrow regenerate myocardium after myocardial infarction, *J. Clin. Invest.* 115:326 (2005).

Zhu et al., Systemic Gene Expression After Intravenous DNA Delivery into Adult Mice, *Science*, 261:209-211 (1993).

Zsebo et al., Stem Cell Factor Is Encoded at the Si Locus of the Mouse and Is the Ligand for the c-kit Tyrosine Kinase Receptor, Cell, 63:213-224, (1980).

International Search report for PCT Patent Application No. PCT/US2006/043937.

Kuhlmann et al., G-CSF/SCF reduces inducible arrythmias in the infracted heart potentially via increased connexin43 expression and arteriogenesis. Journal of Experimental Medicine, 203(1): p. 87-97, 2006.

Patella et al., Stem cell factor in mast cells and increased mast cell density in idiopathic and ischemic cardiomyopathy. Circulation, 97(10): p. 971-978, 1998.

Supplementary European Search Report for EPO Patent Application No. 06 82 7745.8 dated Mar. 26, 2010.

Office Action dated Mar. 13, 2012 for JP application No. 2008540240 in English language translation.

Orlic et al, Mobilized bone marrow cells repair the infarcted heart, improving function and survival, Proceed Nat. Acad. Sciences vol. 98, No. 18:10344-10349.

Sesti et al, Granulocyte Colony-Stimulating Factor and Stem Cell Factor Improve Contractile Reserve of the Infarcted Left Ventricle Independent of Restoring Muscle Mass, J. Amer. Coll. Card., vol. 46, No. 9:1662-1669 (2005).

European Office Action dated Jul. 13, 2012 for EP Application No. 06 827 745.8-2401.

* cited by examiner

FIGURE 1

```
         10         20         30         40         50         60
MKKTQTWILT CIYLQLLLFN PLVKTEGICR NRVTNNVKDV TKLVANLPKD YMITLKYVPG 70         80         90        100        110        120
MDVLPSHCWI SEMVVQLSDS LTDLLDKFSN ISEGLSNYSI IDKLVNIVDD LVECVKENSS 130        140        150        160        170        180
KDLKKSFKSP EPRLFTPEEF FRIFNRSIDA FKDFVVASET SDCVVSSTLS PEKDSRVSVT 190        200        210        220        230        240
KPFMLPPVAA SSLRNDSSSS NRKAKNPPGD SSLHWAAMAL PALFSLIIGF AFGALYWKKR 250        260        270
QPSLTRAVEN IQINEEDNEI SMLQEKEREF QEV
```

FIGURE 2

```
  1  acaccactgt ttgtgctgga tcgcagcgct gcctttcctt atgaagaaga cacaaacttg
 61  gattctcact tgcatttatc ttcagctgct cctatttaat cctctcgtca aaactgaagg
121  gatctgcagg aatcgtgtga ctaataatgt aaaagacgtc actaaattgg tggcaaatct
181  tccaaaagac tacatgataa ccctcaaata tgtccccggg atggatgttt tgccaagtca
241  ttgtttggata agcgagatgg tagtacaatt gtcagacagc ttgactgatc ttctggacaa
301  gtttcaaat atttctgaag gcttgagtaa ttattccatc atagacaaac ttgtgaatat
361  agtggatgac cttgtgggagt gcgtgaaaga aaactcatct aaggatctaa aaaaatcatt
421  caagagccca gaacccaggc tctttactcc tgaagaattc tttagaattt ttaatagatc
481  cattgatgcc ttcaaggact ttgtagtggc atctgaaact agtgattgtg tggtttcttc
541  aacattaagt cctgagaaag attccagagt cagtgtcaca aaaccattta tgttaccccc
601  tgttgcagcc agctccctta ggaatgacag cagtagcagt aataggaagg ccaaaaatcc
661  ccctggagac tccagcctac actgggcagc catggcattg ccagcattgt ttctctcttat
721  aattggcttt gcttttggag ccttatactg gaagaagaga cagccaagtc ttacaagggc
781  agttgaaaat atacaaatta atgaagagga taatgagata agtatgttgc aagagaaaga
841  gagagagttt caagaagtgt aattgtggct tgtatcaaca ctgttacttt cgtacattgg
901  ctggtaaca
```

MEMBRANE BOUND STEM CELL FACTOR THERAPY FOR ISCHEMIC HEART

This application claims priority to U.S. Provisional Patent Application Ser. No. 60/737,058 filed Nov. 14, 2005, the entire contents of which are incorporated by reference herein.

FIELD OF THE INVENTION

The present invention relates to the use of human Stem Cell Factor (SCF) for the treatment of ischemic tissue injury. The present invention also relates to vectors and delivery methods for expressing SCF polypeptides in vivo.

BACKGROUND OF THE INVENTION

The following discussion of the background of the invention is merely provided to aid the reader in understanding the invention and is not admitted to describe or constitute prior art to the present invention.

Stem cell therapy has become an active area of research in cardiology following the demonstration that these cells play a role in neovascularization and possibly in improvement of cardiac function following myocardial infarction. Stem cells also have shown promise in preclinical and clinical studies for the treatment of ischemic syndromes such as coronary artery disease, congestive heart failure, and peripheral artery disease. See Perin, et. al., Circulation 2003 107:r75-r83; Haider, et al., J. Mol. Cell. Cardiol. 2005 38(2):225; Deschaseaux, et. al., Cardiovascular Res. 2005 65(2):305; Thompson, et. al., J. Heart Lung Transplant. 2005 24(2):2051; US Patent Application publication No. 20060008450. Methods for efficient expansion of stem cells in culture have been described. See Feugier et al., J. Hematotherapy and Stem Cell Res. 2002 11:127-138.

Several mechanisms of action have been postulated for stem cell derived therapeutic effects in these disease models; 1) Endothelial precursors present in preparations of bone marrow stem cells induce neovascularization in ischemic tissue and that this neovascularization enhances blood flow which prevents apoptosis of damaged cells and promotes tissue repair. See Itescu, J. Mol. Med. 2003 81 (5):288; Orlic, Proc. Natl. Acad. Sci. (USA) 2001 98:10344; 2) Bone marrow derived stem cells induce endogenous cardiomyocytogenesis. See Yoon, et. al. J. Clin. Invest. 2005 115:326; 3) Mammalian cells have been shown to be capable of building nanotubular "highways" between stem cells and cardiomyocytes, and cytoplasmic organelles and fluids are transported into the cardiomyocytes. See Koyanagi, et al., Circulation Res. 200596:1039-1041; and 4) Paracrine (humoral) factors secreted by bone marrow derived cells promote cardiomyocyte survival. See Gnecchi, et al., Nat. Med. 2005 11:367-368.

Direct injection of CD34+ bone marrow stem cells or autologous myoblasts has been found to improve clinical outcome in ischemic diseases such as post myocardial infarction. However, ex-vivo processing of cells poses significant technical challenges such as lack of adequate modes of high efficiency delivery. See Takagi, et al. J. Biosci Bioengineer. 2005 99:189-196. In addition, there is a complicated regulatory network for the manufacturing of cell products involving maintenance of adequate sterility, cold chain transport, quality control testing logistics, etc. (Bosse, et al., Ann Hematol 2005 79:469-476. Finally, injection of non-cardiac cells into the heart may cause arrhythmia which can be life threatening. See Menasche, et al., J. Am. Coll. Cardiol. 2003 41(7):1078-1083.

The administration of particular cytokines such as SCF and G-CSF have been shown to enhance recovery of heart function following acute myocardial infarction. See Orlic et al., Proc. Natl. Acad. Sci (USA) 2001 98(18):10344-10349; Takano et al., Current Pharmaceutical Design 2003 9:1121-1127; Ohtsuka et al., The FASEB J. 2004 18(7):851-3. Administration of adenoviral vectors encoding VEGF165, VEGF189, ANG-1 or SDF-1, has been used to increase plasma levels of hematopoietic stem cells and endothelial progenitors. Rafii et al., Gene Therapy 2002 9:631-641.

Stem cell factor ("SCF") is a ligand for the tyrosine kinase receptor known as c-kit. See Zsebo, Cell 1990, 63 (1) 213-24); U.S. Pat. No. 6,218,148. SCF induces the proliferation of primitive CD34+ bone marrow progenitors. It has been shown in a number of studies in mice, dogs, and humans, that the SCF/c-kit pathway is involved in the normal process of repair following ischemic damage. Mice genetically deficient in c-kit signaling, has shown that recovery after myocardial infarction depends on SCF induced proliferation of c-kit+ cells in the heart. See Fazel, et. al. "Stem cell factor receptor and cardiac regeneration after myocardial infarction" Am. Heart Assoc. Scientific Sessions 2004, Circulation 2004 Oct. 26; 110(17 Suppl) abstract no. 2182; Ayach, et al., "c-Kit$^+$ BM cells are essential for reducing deteriorating myocardial and heart function post-myocardial infarction" Am. Heart Assoc. Scientific Sessions 2004, Circulation 2004 Oct. 26; 110(17 Suppl) abstract no. 317. SCF is induced in canine cardiac tissue after myocardial infarction. See Frangogiannis, et al., Circulation 1998 98:687. SCF mRNA is induced within 72 hours of reperfusion following myocardial infarction See Frangogiannis et al 1998. SCF production from infracted myocardium has been traced to a subset of macrophages resident therein, and increased density of c-kit+ mast cells at the ischemic site. Mast cells can secrete angiogenic factors such as vascular endothelial growth factor (VEGF), which promote the revascularization process. See Heissig, et al., J. Exp. Med. 2005 202(6):739-50. SCF expression was found to be decreased in the heart following myocardial infarction. See Woldbaek, et. al., Acta Physiol Scand 2002 175:173-181. In vitro studies showed that SCF gene expression can be suppressed by proinflammatory cytokines including TNF-A. See Andrews, et al., 1992 Blood 80:365 A; Langley, Blood, 1993 81:656-660.

U.S. Pat. No. 6,723,561 describes retroviral vectors encoding SCF and retroviral packaging cell lines expressing SCF and use of same to deliver a foreign nucleic acid to stem cells in a subject.

SUMMARY OF THE INVENTION

Described are methods for the treatment of injury in a subject. The method involves delivery of a nucleic acid encoding SCF to the site of injury in the subject where it is taken up by cells which express SCF from the nucleic acid. The form of SCF encoded by the nucleic acid may be a membrane bound form, a secretable form or both. Following administration and uptake by cells at the site of injury, the expressed SCF may recruit c-kit expressing stem cells and/or mast cells in the body to the site of the injury to effect repair of the damaged tissue.

It should be understood that the nucleic acid can be delivered as a soluble molecule, alone or in association with proteins, lipids and other substances, as part of a virus, or encapsulated within an artificial particle such as a liposome. The nucleic acid, however, is not delivered within a cell. However, it should be understood that cells may be administered separate and apart from the administration of the nucleic acid.

Such administered cells may include stem cells. The method, however, does not require the administration of any such cells.

Injuries subject to the method of treatment include ischemic injuries. As used herein, "ischemic injury" refers to tissue damage resulting from inadequate blood supply to the tissue, such as caused by arterial narrowing or blockage. Severe ischemia may lead to necrosis of the tissue. Treatment of ischemic tissue as used herein refers to reducing the severity of an injury to tissue resulting from an ischemic insult.

Preferably the ischemic injury is associated with the cardiovascular system. Ischemic injuries involving the cardiovascular system that can be treated by the methods disclosed herein include myocardial infarction, ischemic stroke, coronary artery disease, peripheral vascular disease (e.g., peripheral artery disease), and congestive heart failure. Other injuries amenable to treatment include peripheral neuropathy, reconstruction surgery and wound healing, and other diseases that are characterized with reduced levels of SCF as part of the injury process. Injuries excluded from the invention include neurological injuries to the central nervous system of a subject.

SCF encoded by the administered nucleic acid is preferably a human SCF. The encoded SCF may be a secretable from of SCF. A preferred secretable form of SCF comprises amino acids 26-165 of FIG. 1. The encoded SCF also may be a membrane bound form of SCF. A preferred membrane bound form of SCF comprises amino acids 25-245 of FIG. 1. Also included is the administration of nucleic acid that encodes a membrane bound form of an SCF and a secretable form of an SCF. As is well known in the art, the nucleic acid encoding each form may be present in a single nucleic acid or may be present in different nucleic acids.

The SCF encoding nucleic acid can be in the form of an expression vector, which may be a viral vector or non-viral vector. Preferred viral vectors include those derived from adenovirus, retrovirus, herpes simplex virus, bovine papilloma virus, adeno-associated virus, lentiviral vector, vaccinia virus, or polyoma virus.

The administered nucleic acid may be delivered to the site of the injury by a use of a receptor for a ligand present in the injured tissue. Viral vector-mediated transduction using targeting moieties has been described for a number of viral vector systems including lentiviruses, retroviruses, adenoviruses, adeno-associated virus and HSV-1 amplicons. See e.g., Takada et al., Rev. Med. Virol. 2003 13:387-398. Alternatively, or in addition, the nucleic acid may be administered to the site of injury with the aid of a device such as a steerable catheter. In one embodiment, the catheter is used to deliver the nucleic acid to ischemic heart tissue. In another embodiment, the nucleic acid is delivered to ischemic heart tissue by way of a device implanted in a wall of the heart. In yet another embodiment, the nucleic acid is delivered to the coronary arterial circulation which then brings the nucleic acid into contact with ischemic heart tissue.

The method of treatment also may include administering stem cells to the subject. Administered stem cells are preferably hematopoietic or mesenchymal. Stem cells may be exogenous stem cells or endogenous stem cells that are generated ex vivo from a cell source of the subject, and then returned to the subject.

The method of treatment also may include administering one or more cytokines or chemokines to the subject. Cytokines or chemokines may be administered in combination with stem cells.

BRIEF DESCRIPTION OF THE DRAWINGS

FIG. 1 is the native amino acid sequence of the a full length human SCF (SEQ ID NO: 1).

FIG. 2 shows a nucleic acid sequence encoding a full length human SCF (SEQ ID NO: 2). The methionine start codon is shown with emphasis starting at nucleotide position 41 and the stop codon TAA is shown with emphasis beginning at position nucleotide 860.

DETAILED DESCRIPTION OF THE PREFERRED EMBODIMENTS

Provided herein are methods for treating a subject suffering from an injury, such as an ischemic injury, comprising administering to the subject a nucleic acid encoding SCF, wherein the nucleic acid is delivered to the site of the injury and is incorporated into cells which express SCF. As discussed, the method of treatment does not require administration of cells to the subject. It is believed that SCF produced at the site of the injury in accordance with the invention methods mobilizes c-kit expressing stem cells and/or mast cells from sites in the body such as the bone marrow which then home to the site of injury. Cells may home to the site of injury and attach to stromal cells therein by any of various receptor/ligand pairs known to be expressed on the stem cells and the stroma. Such receptor/ligand pairs may include SCF/c-kit, SDF-1/CXCR4, and VCAM-1/VLA-4. See Cottler-Fox, et. al., Am. Soc. Hematol. Educ. Program Book 2003 San Diego Calif., page 419.

Targeted delivery of SCF to the site of an injury as described herein also may enhance the number of c-kit expressing cells circulating in blood mobilized from the bone marrow, and assist such cells in targeting to ischemic tissue. Targeted delivery of SCF to the sites of injury as described herein also may increase the proliferation of the engrafted cells. Any or all of these results may occur following targeting of SCF nucleic acid to the site of an injury.

As used herein delivery to the "site of an injury" means that the nucleic acid encoding SCF is delivered to cells present within injured tissue. One skilled in the art appreciates that to deliver to the site of an injury does not require that all of the administered nucleic acid is delivered to the injured tissue site or that none of the administered nucleic acid not delivered to cells outside the injured site. Administered nucleic acid can be taken up and expressed by cells in the body outside of the injured tissue provided that the amount of SCF which is expressed by cells within the injured tissue is sufficient to recruit stem cells to the site of injury and provide therapeutic improvement. It should be understood that reference herein to administering a nucleic acid encoding SCF is not limited to administering naked nucleic acid but also includes administering the nucleic acid in association with proteins, lipids and other substances. Accordingly, the administered nucleic acid can be a viral vector which may be packaged within a viral particle, a nucleic acid associated with a liposome, and the like.

SCF therapy as described herein can be a stand alone treatment, may be combined with standard medical management, or may be combined with other specialized therapy such as the administration of cytokines, chemokines and/or stem cells.

In preferred approaches the injury is an ischemic injury associated with the cardiovascular system. The term "cardiovascular disorder" as used herein refers to abnormalities of the heart and vasculature. The term is intended to include, but is not limited to, renovascular hypertension, congestive heart failure, aortic aneurysm, iliac or femoral aneurysm, pulmonary embolism, myocardial infarction, acute coronary syndrome, angina, primary hypertension, atrial fibrillation, systolic dysfunction, diastolic dysfunction, myocarditis, atherosclerosis, atrial tachycardia, ventricular fibrillation, endocarditis, and peripheral vascular disease. Cardiovascular conditions resulting from ischemia such as coronary artery disease, congestive heart failure, and peripheral artery disease are particularly amendable to treatment using the invention methods. In accordance with the methods herein, treatment of a cardiovascular system injury such as involving the heart or peripheral sites such as the leg is accomplished by methods in which the SCF encoding nucleic acid is delivered to the site of injury.

As used herein, "stem cell factor" or "SCF" or "SCF polypeptide" refers to naturally-occurring SCF (e.g. natural human SCF) as well as non-naturally occurring (i.e., different from naturally occurring) polypeptides having amino acid sequences and glycosylation sufficiently duplicative of that of naturally-occurring stem cell factor so as to retain at least one biological activity of the naturally-occurring stem cell factor. Biological activity of SCF includes the stimulation of growth of early hematopoietic progenitors which are capable of maturing to erythroid, megakaryocyte, granulocyte, lymphocyte, and macrophage cells. SCF also functions to increases the numbers of hematopoietic cells of both myeloid and lymphoid lineages in animals following administration of SCF. One of the hallmark characteristics of stem cells is their ability to differentiate into both myeloid and lymphoid cells. See Spangrude, et al., Science 1988 241: 58-62.

An SCF polypeptide can be the full-length native polypeptide or a variant of the sequence. See e.g., Martin, F H. Cell, 1990, 63, 203-211; U.S. Pat. No. 6,218,148. An SCF polypeptide may also encompass truncated or secreted forms of an SCF polypeptide, (e.g., soluble forms containing an extracellular domain sequence), variant forms (e.g., alternatively spliced forms) and allelic variants of an SCF polypeptide.

A full length native SCF polypeptide is produced as a 273 amino acid precursor, which comprises residues 1-25 as the signal sequence, residues 26-214 as the extracellular domain, residues 215-237 as a potential transmembrane domain and residues 238-273 as a potential cytoplasmic domain. See Swiss-Prot entry P21583 or FIG. 1. Nucleotide sequence encoding a full-length native human SCF is shown in FIG. 2 as nt positions 41-862 (see also GenBank accession no. BC074725). Nucleic acid sequences encoding splice variants of SCF are found in GenBank under accession no. NM_000899 and NM_003994.2. Thus, a human native SCF represents 248 amino acids from positions 26-273 of Swiss-Prot entry P21583 or FIG. 1. Shorter versions of the native human SCF include a membrane bound form representing positions 26-245 of Swiss-Prot entry P21583 or FIG. 1 and a soluble version representing positions 26-165 of Swiss-Prot entry P21583 or FIG. 1.

As used herein, "soluble SCF" or "secretable SCF" refers to a form of SCF that has biological activity with respect to the c-kit but which that lacks a functional transmembrane domain. Secretable forms of SCF which lack a functional transmembrane domain are missing all or nearly all of the sequence from 238-273 of Swiss-Prot entry P21583 or FIG. 1. A "functional transmembrane domain" is one which when included in a protein retains the protein in the plasma membrane of a cell that produces the protein. A soluble or secretable SCF can be maintained in an aqueous solution without the addition of detergent.

SCF as used herein include variants of SCF polypeptides ("variant SCF polypeptides") which refer to an "active" SCF polypeptide, wherein activity is as defined herein, and having at least about 95% amino acid sequence identity with the native human SCF polypeptide sequence. Such SCF polypeptide variants include, for instance, SCF polypeptides wherein one or more amino acid residues are added, substituted or deleted at the N- or C-terminus or within the sequence. Ordinarily, variant SCF polypeptides will have at least about 95% amino acid sequence identity, more preferably at least about 95% sequence identity, 96%, 97%, 98%, 99% or greater than 99% sequence identity sequence identity with the native amino acid sequence described, with or without the signal peptide. Natural and nonnatural SCF polypeptides are also described in U.S. Pat. No. 6,759,215 or 6,207,417.

SCF polypeptides also may include pre- or pro-proteins or mature proteins, including polypeptides or proteins that are capable of being directed to the endoplasmic reticulum (ER), a secretory vesicle, a cellular compartment, or an extracellular space typically, e.g., as a result of a signal sequence, however, proteins released into an extracellular space without necessarily having a signal sequence are also encompassed. Generally, the polypeptides undergo processing, e.g., cleavage of a signal sequence, modification, folding, etc., resulting in a mature form (see, e.g., Alberts, et al. (1994) Molecular Biology of The Cell, Garland Publishing, New York, N.Y., pp. 557-592). If an SCF polypeptide is released into the extracellular space, it can undergo extracellular processing to produce a "mature" protein. Release into the extracellular space can occur by many mechanisms, including, e.g., exocytosis, and proteolytic cleavage.

SCF polypeptides may also be "altered," resulting in "variations," and may contain deletions, insertions, or substitutions of amino acid residues that produce a silent change and result in functionally equivalent proteins. Deliberate amino acid substitutions may be made based on similarity in polarity, charge, solubility, hydrophobicity, hydrophilicity, and/or the amphipathic nature of the residues, as long as the biological or immunological activity of the SCF polypeptide is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

SCF polypeptides can be prepared in any manner known in the art. For example, naturally occurring SCF polypeptides can be isolated, recombinantly produced, synthetically produced, or produced by any combination of these methods. For example, a recombinantly produced version of an SCF polypeptide, including a secreted polypeptide, can be purified using techniques described herein or otherwise known in the art. See Martin F H, et. al., Primary structure and functional expression of rat and human stem cell factor DNAs. Cell 63:203, 1990. An SCF polypeptide also may be purified from natural, synthetic or recombinant sources or otherwise known in the art, such as, e.g., using an antibody raised against SCF or a peptide sequence fused to SCF. See, e.g., U.S. Pat. No. 6,759,215 or 6,207,417.

SCF polypeptides and variants described herein are encoded by nucleic acid. The encoding SCF polynucleotide sequences Ordinarily, an SCF polynucleotide variant will have at least about 75% nucleic acid sequence identity, more preferably at least about 80% nucleic acid sequence identity, yet more preferably at least about 81% nucleic acid sequence identity, yet more preferably at least about 82% nucleic acid sequence identity, yet more preferably at least about 83% nucleic acid sequence identity, yet more preferably at least about 84% nucleic acid sequence identity, yet more preferably at least about 85% nucleic acid sequence identity, yet more preferably at least about 86% nucleic acid sequence identity, yet more preferably at least about 87% nucleic acid sequence identity, yet more preferably at least about 88% nucleic acid sequence identity, yet more preferably at least about 89% nucleic acid sequence identity, yet more preferably at least about 90% nucleic acid sequence identity, yet more preferably at least about 91% nucleic acid sequence identity, yet more preferably at least about 92% nucleic acid sequence identity, yet more preferably at least about 93% nucleic acid sequence identity, yet more preferably at least about 94% nucleic acid sequence identity, yet more preferably at least about 95% nucleic acid sequence identity, yet more preferably at least about 96% nucleic acid sequence identity, yet more preferably at least about 97% nucleic acid sequence identity, yet more preferably at least about 98% nucleic acid sequence identity, yet more preferably at least about 99% nucleic acid sequence identity with a native SCF nucleic acid sequence. Preferably, the variants will have at least about 95%, more preferably at least 96%, 97%, 98%, 99% or greater than 99% sequence identity to the native polynucleotide sequence. See Martin, F H. Primary Structure And Functional Expression Of Rat And Human Stem-Cell Factor DNAS Cell, 1990, 63, 203-211. It will be appreciated by those skilled in the art that as a result of the degeneracy of the genetic code, a multitude of polynucleotide sequences encoding SCF polypeptides, some bearing minimal homology to the polynucleotide sequences of any known and naturally occurring gene may be produced. Thus, the SCF encoding nucleic acid contemplates each and every possible variation of polynucleotide sequence that could be made by selecting combinations based on possible codon choices. These combinations are made in accordance with the standard triplet genetic code as applied to the polynucleotide sequences of naturally occurring SCF, and all such variations are to be considered as being specifically disclosed. DNA sequence encoding natural and nonnatural SCF polypeptides are described in U.S. Pat. No. 6,759,215 or 6,207,417.

The encoding polynucleotide may be prepared by synthetic chemistry. After production, the synthetic sequence may be used alone or inserted into any of the many available expression vectors and cell systems using reagents that are well known in the art. Moreover, synthetic chemistry may be used to introduce mutations into a sequence encoding SCF.

An encoding SCF polynucleotide can be composed of polyribonucleotide or polydeoxyribonucleotide, which may be unmodified RNA or DNA or modified RNA or DNA. For example, the SCF polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, an encoding SCF polynucleotides can be composed of triple-stranded regions comprising RNA or DNA or both RNA and DNA. SCF polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The term "similar" or "similarity" as used herein describes the relationship between different nucleic acid or amino acid sequences in which the sequences are related by partial sequence identity or sequence similarity at one or more blocks or regions within the sequence. Such similar amino acid residues may be either identical between different amino acid sequences, or represent conservative amino acid substitutions between different sequences. Accordingly, the term "identity" describes amino acid residues, which are identical between different amino acid sequences. Amino acid sequence similarity or identity with respect to each SCF amino acid sequence identified herein is defined as the percentage of amino acid residues in a candidate sequence that are similar or identical with the amino acid residues in an SCF polypeptide sequence, after aligning the sequences and introducing gaps, if necessary, to achieve the maximum percent sequence similarity or identity. "Percent (%) amino acid sequence identity" with respect to the SCF amino acid sequences identified herein is defined as the percentage of amino acid residues in a candidate sequence that are identical with the amino acid residues in an SCF polypeptide sequence, after aligning the sequences and introducing gaps, if necessary, to achieve the maximum percent sequence identity, and not considering any conservative substitutions as part of the sequence identity. Likewise, "Percent (%) nucleic acid sequence identity" with respect to the SCF polynucleotide sequences identified herein is defined as the percentage of nucleotides in a candidate sequence that are identical with the nucleotides in the SCF polynucleotide sequence after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as ALIGN, ALIGN-2, Megalign (DNASTAR) or BLAST (e.g., Blast, Blast-2, WU-Blast-2) software and using default settings for gap penalty and the like. Those skilled in the art can determine appropriate parameters for measuring alignment, including any algorithms needed to achieve maximal alignment over the full length of the sequences being compared. For example, the percent identity values used herein are generated using WU-BLAST-2 [Altschul, et al., *Methods in Enzymology* 266:460-80 (1996)]. Most of the WU-BLAST-2 search parameters are set to the default values. Those not set to default values, i.e., the adjustable parameters, are set with the following values: overlap span=1; overlap fraction=0.125; word threshold (T)=11; and scoring matrix=BLOSUM 62. For purposes herein, a percent amino acid sequence identity value is determined by dividing (a) the number of matching identical amino acid residues between the amino acid sequence of the SCF polypeptide of interest and the comparison amino acid sequence of interest (i.e., the sequence against which the SCF polypeptide of interest is being compared) as determined by WU-BLAST-2, by (b) the total number of amino acid residues of the SCF polypeptide of interest, respectively.

An indication that two nucleic acid sequences are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions as is well known in the art. Exemplary high stringency conditions include low salt concentrations (e.g., <4×SSC buffer and/or <2×SSC buffer), the presence of non-ionic detergent (e.g., 0.1% SDS), and/or relatively high temperatures (e.g., >55° C. and/or >70° C.).

In other embodiments, the SCF variant polypeptides are encoded by nucleic acid molecules which are capable of hybridizing, preferably under stringent hybridization and wash conditions, to nucleotide sequences encoding the full-length SCF native polypeptide. The term "mature protein" or "mature polypeptide" as used herein refers to the form(s) of the protein produced by expression in a mammalian cell. It is generally hypothesized that once export of a growing protein chain across the rough endoplasmic reticulum has been initiated, proteins secreted by mammalian cells have a signal peptide (SP) sequence which is cleaved from the complete polypeptide to produce a "mature" form of the protein. Cleavage of a secreted protein is not often uniform and may result in more than one species of mature protein. The cleavage site of a secreted protein is determined from the primary amino acid sequence of the complete protein.

As used herein, the term "vector" means a non-chromosomal nucleic acid comprising an intact replicon such that the vector may be replicated when placed within a cell, for example by a process of transformation. Viral vectors include retroviruses, adenoviruses, herpesvirus, papovirus, or otherwise modified naturally occurring viruses. Vector also means a formulation of nucleic acid with a chemical or substance which allows uptake by cells. Advances in biochemistry and molecular biology in recent years have led to the construction of recombinant vectors in which, for example, retroviruses, adenoviruses and plasmids are made to contain exogenous RNA or DNA respectively. In particular instances the recombinant vector can include heterologous RNA or DNA.

Vectors for delivering nucleic acids can be viral, non-viral, or physical. See, for example, Rosenberg et al., *Science*, 242: 1575-1578 (1988), and Wolff et al., *Proc. Natl. Acad. Sci. USA* 86:9011-9014 (1989). Recent reviews discussing methods and compositions for use in gene therapy include Eck et al., in *Goodman & Gilman's The Pharmacological Basis of Therapeutics*, Ninth Edition, Hardman et al., eds., McGraw-Hill, New York, (1996), Chapter 5, pp. 77-101; Wilson, *Clin. Exp. Immunol.* 107 (Suppl. 1):31-32 (1997); Wivel et al., *Hematology/Oncology Clinics of North America, Gene Therapy*, S. L. Eck, ed., 12(3):483-501 (1998); Romano et al., *Stem Cells*, 18:19-39 (2000), and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, and adeno-associated virus vectors.

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA can provide long-term expression in muscle. See Wolff, et al., Human Mol. Genet., 1992 1:363-369; Wolff, et al., Science, 1990 247, 1465-1468. DNA-mediated gene transfer has also been characterized in liver, heart, lung, brain and endothelial cells. See Zhu, et al., Science, 1993 261: 209-211; Nabel, et al., Science, 1989 244:1342-1344. DNA for gene transfer also may be used in association with various cationic lipids, polycations and other conjugating substances. See Przybylska et al., J. Gene Med., 2004 6: 85-92; Svahn, et al., J. Gene Med., 2004 6: S36-S44.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences are functionally linked and in some cases contiguous such as a secretory leader, which is contiguous also in reading frame. However enhancers do not have to be contiguous. Linking is accomplished by ligation at convenient restriction sites. If such sites do not exist, the synthetic oligonucleotide adapters or linkers are used in accordance with conventional practice.

The techniques for introducing nucleic acids into cells vary depending upon whether the nucleic acid is transferred into cultured cells in vitro or in vivo into cells of the intended host. Techniques suitable for the transfer of nucleic acid into mammalian cells in vitro include the use of liposomes, electroporation, microinjection, cell fusion, DEAE-dextran, the calcium phosphate precipitation method, and the like. Preferred in vivo gene transfer techniques include transfection with viral (typically, retroviral or adenoviral) vectors and viral coat protein-liposome mediated transfection (Dzau, et al., *Trends in Biotechnology* 11 (5):205-10 (1993)). Suitable vectors can be constructed by any of the methods well known in the art. See, for example, Sambrook et al., *Molecular Cloning, A Laboratory Manual*, Second Edition, Cold Spring Harbor Press (1989), and Ausubel et al., eds., *Current Protocols in Molecular Biology*, John Wiley & Sons, N.Y. (1987 and updates); Moore, et al., Ann N Y Acad Sci. 2001 938:36-45-47. The use of cationic liposomes, such as the CD-Chol/DOPE liposome, has been widely documented as an appropriate vehicle to deliver DNA to a wide range of tissues through intravenous injection of DNA/cationic liposome complexes. See Caplen et al., *Nature Med.*, 1:39-46 (1995); Zhu et al., *Science*, 261:209-211 (1993). Liposome transfer of genes to target cells by fusing with the plasma membrane. Examples of the successful application of liposome complexes include those of Lesson-Wood et al., *Human Gene Therapy*, 6:395-405 (1995), and Xu et al., *Molecular Genetics and Metabolism*, 63:103-109 (1998).

Nucleic acid is delivered to the site of the injury in an subject by any of various means known in the art. Delivery to a site may be achieved by a receptor/ligand mediated approach. such as an antibody specific for a cell surface membrane protein or the target cell, a ligand for a receptor on the target cells, and the like. Where liposomes are employed, proteins which bind to a cell surface membrane protein associated with endocytosis may by used for targeting and/or to facilitate uptake, e.g., capsid proteins or fragments thereof trophic for a particular cell type, antibodies for proteins which undergo internalization in cycling, proteins that target intracellular localization and enhance intracellular half-life. The technique of receptor-mediated endocytosis is described, for example, by Wu, et al., *J. Biol. Chem.* 262(10):4429-32 (1987); and Wagner, et al., *Proc. Natl. Acad. Sci. USA* 87(9): 3410-4 (1990). For a review of gene marking and gene therapy protocols, see Anderson, *Science* 256(5058):808-13 (1992).

Nucleic acid may be delivered to the site of the injury in an subject with the assistance of a mechanical device such as a catheter. For example, when the heart is damaged, nucleic acid may be delivered to interstitial regions of the myocardium as described by Altman et al., U.S. Patent Publication no. 20020010462. Essentially, a steerable catheter is advanced to a location within the heart chamber and placed adjacent to the heart wall. The drug delivery catheter is advanced so that it penetrates the heart wall and the desired volume of particulate delivery slurry or suspension (0.05 ml to 2.0 ml) is infused. The penetrating structure would be disengaged, and the drug delivery catheter is pulled back a short distance within the delivery catheter. The steerable catheter is then in reposition, and the process is repeated a number of times as desired. In this method, delivery is via a catheter system that delivers a stable liposomal preparation containing a vector for expressing an SCF polypeptide. This approach also may be used target SCF encoding nucleic acid to or others region of the cardiovascular system.

A sustained-release delivery technology in the form of miniature pumps and/or in the form of depots and implants as described by Struijker-Boudier et al., U.S. Patent Publication 20030009145, can be used to deliver SCF encoding nucleic acid to the heart or other region of the cardiovascular system. In accordance with the method, a pump is generally implanted subcutaneously, for example in the chest wall or under the arm, and is connected to a catheter to deliver the vector, where the distal end of the catheter is implanted into cardiac tissue and held in place by sutures. Additionally, a non-polymeric depot that can be injected into a tissue to effect sustained release of the vector locally, producing highly effective local concentrations of the vector but without the undesirable sire-effects of systemic drug delivery. The non-polymeric depot, having released the vector for the desired period, is slowly degraded by the body, overcoming the need to remove the delivery device.

SCF encoding nucleic acid can be delivered to damaged heart tissue by direct epicardial infusion in the coronary circulation. This work is described in U.S. provisional application Ser. No. 60/833,324 titled "Extended antegrade epicardial coronary infusion of adeno-associated viral vectors for gene therapy" filed 25 Jul. 2006. Briefly, the nucleic acid, e.g. polynucleotide/viral vector as described in more detail herein, is administered to the subject by infusion into a blood vessel of the coronary circulation of the beating heart in vivo for a period of at least about three minutes in a particular blood vessel. Of the four main coronary arteries providing oxygenated blood to the heart for distribution throughout the heart tissue (i.e., the left main and right coronary arteries, the left anterior descending artery, and the left circumflex artery), one or more may be infused with the nucleic acid, for example infusion of the left and right coronary arteries. The period for infusion may be for 8 minutes, 10 minutes, or even longer. Preferably, the antegrade, epicardial infusion of the left and right main coronary arteries is used. Also contemplated is retrograde infusion of a coronary artery, or a combination of one or more antegrade and retrograde coronary arteries or veins. The infusion flow rate can vary from about 0.1 mL/min to 10 mL/min. In preferred embodiments, the flow rate is between about 0.2 mL/min and about 6.0 mL/min., more preferably between about 0.2 mL/min and about 2.5 mL/min., more preferably between about 0.2 mL/min. and about 2.0 mL/min. Infusion of the coronary blood vessel(s) is performed using standard guidewires, catheters and infusion pumps. In a preferred embodiment, the infusion catheter is directed to the coronary artery under fluoroscopic guidance via the femoral artery. As used herein, "blood vessel of the coronary circulation," "coronary blood vessel" or "blood vessel of the heart" includes grafts onto coronary blood vessels, for example those resulting from bypass surgery. As used herein, "epicardial" refers to blood vessels located on the outer portion of the heart, e.g. the left or right coronary arteries. It is noted that this approach does not require isolation of the coronary circulation from the systemic circulation or otherwise re-circulate the nucleic acid, or to artificially restrict the coronary venous circulation as a means to increase pressure within the coronary circulation or to increase dwell time of the nucleic acid.

SCF encoding nucleic acid can be delivered to cardiac tissue by isolating coronary veins, i.e. the coronary venous circulation, substantially or completely from the systemic circulation using V-Focus cardiac circulation device which includes special catheters, an oxygenator and perfusion pump. This and related work is described in U.S. provisional application Ser. No. 60/548,038 titled "Methods for delivering therapeutic agents to heart tissue," filed 26 Feb. 2004; Ser. No. 60/612,846 titled "Isolating cardiac circulation," filed 24 Sep. 2004, and Ser. No. 60/685,913 titled "Polynucleotide delivery to cardiac tissue," filed 31 May 2005, as well as PCT/AU2005/000237 filed Aug. 25, 2005. In accordance with these methods, a polynucleotide introduced into the coronary arterial circulation is thereby selectively delivered to the heart tissue. The polynucleotide may or may not be recirculated from the coronary venous circulation to the coronary arterial circulation. Preferably, the polynucleotide is recirculated. Advantageously, substantial isolation of the coronary venous circulation from the systemic circulation provides for the preferential delivery of a polynucleotide to cardiac tissue, while exposure of non-cardiac tissue to the polynucleotide is minimized. Preferably, the coronary venous circulation is isolated from the systemic circulation by occluding the flow between the coronary sinus and the systemic circulation. Any polynucleotide exiting the coronary venous circulation is therefore restricted from entering the systemic circulation (e.g. the vena cavae or right atrium) for transport to other parts of the body. The method may include use of a venous collection device in the coronary sinus to drain polynucleotide from the cardiac tissue. The venous collection device may include a support to maintain patency of the coronary sinus during collection of fluid therefrom. An artificial flow path is established between the venous collection device and the one or more coronary arteries and the polynucleotide is added to the artificial flow path for delivery to the heart. Preferably, the support structure comprises a two- or three-dimensional framework which is deliverable to the coronary sinus in a compressed state. The framework is expandable upon release of the compressed structure from a delivery lumen to maintain patency within the coronary sinus. The support structure for maintaining patency of the coronary sinus during collection of fluid therefrom is preferably percutaneously deliverable. In another embodiment, the support structure may comprise two consecutively inflatable regions. The first region is configured to, when inflated, rest in abutment with a portion of the right atrium wall surrounding the coronary sinus ostium. The second region is configured to, when inflated, maintain patency of the coronary sinus while flow between the coronary sinus and the right atrium is occluded. These balloon regions may be used with or without a compressible support structure such as the framework described above. The V-Focus system could be used to deliver SCF polypeptides and polynucleotides for the treatment of ischemic cardiac disease, non-ischemic cardiomyopathy, peripheral vascular disease, and aging.

Various other methods and devices which have been developed for delivering therapeutic agents to cardiac tissue can be used to deliver SCF encoding nucleic acid to the site of the injury in an subject. For example, U.S. Pat. Nos. 5,387,419; 5,931,810; 5,827,216; 5,900,433; 5,681,278; and 5,634,895 and PCT Publication No. WO 97/16170 describe various devices and/or methods of delivering agents to the heart by, for example, transpericardial delivery. Also, U.S. Pat. Nos. 5,387,419 and 5,797,870 describe methods for delivery of agents to the heart by admixing the agent with a material to facilitate sustained or controlled release of agent from a device, or by admixing the agent with a viscosity enhancer to maintain prolonged, high pericellular agent concentration.

Methods for site-specific delivery of nucleic acid also include the direct deposition of the nucleic acid into the arterial wall. For example, U.S. Pat. No. 6,251,418 discloses a method for implanting solid polymer pellets into myocardial tissue, where the pellets are coated with or contain a drug. U.S. Pat. No. 6,258,119 describes a myocardial implant for insertion into a heart wall for trans myocardial revascularization (TMR) of the heart wall. The implant provides a means to promote angiogenesis, and has a flexible, elongated body that contains a cavity and openings through the flexible, elongated body from the cavity. The TMR implant includes a coaxial anchoring element integrally formed at one end for securing the TMR implant in the heart wall.

Physical methods for delivery of SCF encoding nucleic acid include the use of needle-free injectors, such as "gene gun" devices, devices using liquid under high pressure for delivery into interstitial spaces, and by electroporation. Administration of SCF encoding nucleic acid to different tissues include muscle injection and peripheral intravenous injections.

Nucleic acid encoding SCF may be prepared and administered intramyocardially as described for delivery of sonic hedgehog encoding nucleic acid as reported by Kusano et al., Nat Med. 2005 11(11):1197-204.

Well-known drug delivery devices that also may be used to deliver nucleic acid to the site of injured cardiovascular tissue include mechanical or electromechanical infusion pumps such as those described in, for example, U.S. Pat. Nos. 4,692, 147; 4,360,019; 4,487,603; 4,360,019; 4,725,852, and the like. Osmotically-driven pumps (such as the DUROST osmotic pump) are described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; 5,985,305; 5,728,396 and WO 97/27840.

The nucleic acid encoding SCF is preferably administered as soon as possible after ischemic insult to optimally enhance revascularization.

For the prevention or treatment of disease, the appropriate dosage of an active agent, will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments. Dosages and desired drug concentration of pharmaceutical compositions may vary depending on the particular use envisioned. The determination of the appropriate dosage or route of administration is well within the skill of an ordinary artisan. Animal experiments provide reliable guidance for the determination of effective does for human therapy.

As used herein, the terms "treating," "treatment," and "therapy" as used herein refer to curative therapy, prophylactic therapy, and preventive therapy. An example of "preventive therapy" is the prevention or lessened targeted pathological condition or disorder. Those in need of treatment include those already with the disorder as well as those prone to have the disorder or those in whom the disorder is to be prevented. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption but, rather, is cyclic in nature. Administration "in combination with" one or more further therapeutic agents includes simultaneous (concurrent) and consecutive administration in any order.

In accordance with the method, SCF encoding nucleic acid may be administered once and achieve a therapeutic effect. Administration of the nucleic acid may be repeated one or more time as needed.

As used herein, a "therapeutically-effective amount" is the minimal amount of active agent (e.g., an SCF polypeptide (or encoding nucleic acid) which is necessary to impart therapeutic benefit to a mammal. For example, a "therapeutically-effective amount" to a mammal suffering or prone to suffering or to prevent it from suffering is such an amount which induces, ameliorates, or otherwise causes an improvement in the pathological symptoms, disease progression, physiological conditions associated with or resistance to succumbing to the aforedescribed disorder.

As used herein, "carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecule weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and PLURONIC.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). The active agent in the composition is typically an SCF polypeptide (or encoding nucleic acid). The label on, or associated with, the container indicates that the composition is used for treating the condition of choice. The article of manufacture may further comprise a second container comprising a pharmaceutically-acceptable buffer, such as phosphate buffered saline, Ringer's solution and dextrose solution. It may further include other materials desirable from a commercial and user standpoint, including other buffers, diluents, filters, needles, syringes, and package inserts with instructions for use.

Methods of treating an ischemic disorder as described herein by administering nucleic acid encoding SCF may also be combined with administration of cells such as stem cells. The cells may be given before, during or after administration of the nucleic acid. Preferably, cells are administered within two weeks of the nucleic acid administration.

Administered cells may be exogenous to the subject and generated in vitro. In another approach, cells may be generated ex vivo from tissue taken from the subject and then returned to the subject during therapy. Methods of generating stem cells ex vivo are well known in the art and include U.S. Pat. Nos. 6,326,198; 6,261,549; 6,093,531; 5,935,565; 5,670,351; 5,670,147; 5,646,043; 5,437,994. These methods are particularly suitable for producing hematopoietic stem cells. Stem cells may cultured and expanded in conjunction with genetically modified cells and with particular cytokines and chemokines such as described by Feugier et al., J. Hematotherapy and Stem Cell Res. 2002 11:127-138.

The treatment of ischemic injury with SCF encoding nucleic acid as described herein also may include administration of mesenchymal stem cells. Such stem cells may be genetically modified to express a cytokine such as SCF as described by Faizel et al., J Thorac Cardiovasc Surg. 2005 130(5):1310.

The treatment of ischemic injury with SCF encoding nucleic acid as described herein may include the administration of one or more cytokines or chemokines. Cytokines or chemokines may be administered as purified protein or as a pharmaceutical formulation of purified protein. Cytokines or chemokines also may be administered by administering an expression that encodes the cytokine so that it is taken up by cells in the subject and the cytokine or chemokine expressed therefrom. A combination of the protein and encoded nucleic acid also may be administered. Two or more cytokines or chemokines may be administered or a combination of both a cytokine and a chemokine may be administered.

As used herein, "cytokine" means any of several regulatory proteins, such as the interleukins and lymphokines, that are released by cells of the immune system and act as intercellular mediators in the generation of an immune response. As used herein "chemokine" refers to a family of structurally related glycoproteins with potent leukocyte activation and/or chemotactic activity. They are 70 to 90 amino acids in length and approximately 8 to 10 kDa in molecular weight. Most of them fit into two subfamilies with four cysteine residues. These subfamilies are base on whether the two amino terminal cysteine residues are immediately adjacent or separated by one amino acid. The a chemokines, also known as CXC chemokines, contain a single amino acid between the first and second cysteine residues; β, or CC, chemokines have adjacent cysteine residues. Most CXC chemokines are chemoattractants for neutrophils whereas CC chemokines generally attract monocytes, lymphocytes, basophils, and eosinophils.

Cytokines and chemokines useful in the therapeutic methods described herein include, for example, granulocyte colony stimulating factor (G-CSF), granulocyte macrophage colony stimulating factor (GM-CSF), SCF, vascular endothelial growth factor family member (VEGF-A to VEGF-E), fibroblast growth factor (FGF), angiopoietin 1 (AdAng1), stromal cell-derived factor 1 (SDF1). These various polypeptides can be produced and administered as is well known in the art or may be introduced as encoding nucleic acid and expressed in vivo. See Orlic et al., Proc. Natl. Acad. Sci (USA) 2001 98(18):10344-10349; Takano et al., Current Pharmaceutical Design 2003 9:1121-1127; Ohtsuka et al., The FASEB J. 2004 18(7):851-3; Rafii et al., Gene Therapy 2002 9:631-641. Many of these polypeptide factors are also available as commercially approved pharmaceuticals (e.g. G-CSF may be purchased as filgrastim or Neupogen (Amgen, Thousand Oaks, Calif.), lenograstim or Granocyte® (Chugai Pharmaceutical Company Ltd.) or pegylated filgrastim or Neulasta® (Amgen, Thousand Oaks, Calif.)).

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

All references, patents, and/or applications cited in the specification are incorporated by reference in their entireties, including any tables and figures, to the same extent as if each reference had been incorporated by reference in its entirety individually.

What is claimed is:

1. A method for treating a subject suffering from an ischemic injury of the heart resulting from myocardial infarction, consisting essentially of administering to the subject a nucleic acid encoding a membrane bound form of stem cell factor (SCF) wherein the nucleic acid is administered to the site of the injury where it is taken up by cells and SCF is expressed, wherein the expression of SCF results in repair of the ischemic injury.

2. The method of claim 1, wherein the SCF comprises amino acids 25-245 of SEQ ID NO:1.

3. The method of claim 1, wherein the SCF is human SCF.

4. The method of claim 1, wherein the nucleic acid is a viral vector.

5. A method for treating a subject suffering from an ischemic injury of the heart resulting from myocardial infarction, comprising administering to the subject a nucleic acid encoding a membrane bound form of stem cell factor (SCF) wherein the nucleic acid is administered to the site of the injury where it is taken up by cells and SCF is expressed, wherein the expression of SCF results in repair of the ischemic injury, and wherein the subject is not administered granulocyte-colony stimulating factor (G-CSF).

6. The method of claim 5, wherein the SCF comprises amino acids 25-245 of SEQ ID NO:1.

7. The method of claim 5, wherein the SCF is human SCF.

8. The method of claim 5, wherein the nucleic acid is a viral vector.

* * * * *

SEQUENCE LISTING

```
<160> NUMBER OF SEQ ID NOS: 2

<210> SEQ ID NO 1
<211> LENGTH: 273
<212> TYPE: PRT
<213> ORGANISM: Homo sapiens

<400> SEQUENCE: 1

Met Lys Lys Thr Gln Thr Trp Ile Leu Thr Cys Ile Tyr Leu Gln Leu
1               5                   10                  15
```

```
Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
 50                  55                  60

Pro Ser His Cys Trp Ile Ser Glu Met Val Val Gln Leu Ser Asp Ser
 65                  70                  75                  80

Leu Thr Asp Leu Leu Asp Lys Phe Ser Asn Ile Ser Glu Gly Leu Ser
                85                  90                  95

Asn Tyr Ser Ile Ile Asp Lys Leu Val Asn Ile Val Asp Leu Val
                100                 105                 110

Glu Cys Val Lys Glu Asn Ser Ser Lys Asp Leu Lys Lys Ser Phe Lys
            115                 120                 125

Ser Pro Glu Pro Arg Leu Phe Thr Pro Glu Glu Phe Phe Arg Ile Phe
    130                 135                 140

Asn Arg Ser Ile Asp Ala Phe Lys Asp Phe Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Lys Asn Pro Pro
    195                 200                 205

Gly Asp Ser Ser Leu His Trp Ala Ala Met Ala Leu Pro Ala Leu Phe
    210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
                260                 265                 270

Val

<210> SEQ ID NO 2
<211> LENGTH: 909
<212> TYPE: DNA
<213> ORGANISM: Homo sapiens

<400> SEQUENCE: 2
acaccactgt tgtgctgga tcgcagcgct gcctttcctt atgaagaaga cacaaacttg    60
gattctcact tgcatttatc ttcagctgct cctatttaat cctctcgtca aaactgaagg   120
gatctgcagg aatcgtgtga ctaataatgt aaaagacgtc actaaattgg tggcaaatct   180
tccaaaagac tacatgataa ccctcaaata tgtccccggg atggatgttt tgccaagtca   240 tgttggata agcgagatgg tagtacaatt gtcagacagc ttgactgatc ttctggacaa   300
gttttcaaat atttctgaag gcttgagtaa ttattccatc atagacaaac ttgtgaatat   360
agtggatgac cttgtggagt gcgtgaaaga aaactcatct aaggatctaa aaaatcatt   420 caagagccca gaaccaggc tctttactcc tgaagaattc tttagaattt ttaatagatc   480
cattgatgcc ttcaaggact tgtagtggc atctgaaact agtgattgtg tggtttcttc   540
aacattaagt cctgagaaag attccagagt cagtgtcaca aaaccattta tgttaccccc   600
tgttgcagcc agctccctta ggaatgacag cagtagcagt aataggaagg ccaaaaatcc   660
```

```
ccctggagac tccagcctac actgggcagc catggcattg ccagcattgt tttctcttat    720
aattggcttt gcttttggag ccttatactg gaagaagaga cagccaagtc ttacaagggc    780
agttgaaaat atacaaatta atgaagagga taatgagata agtatgttgc aagagaaaga    840
gagagagttt caagaagtgt aattgtggct tgtatcaaca ctgttacttt cgtacattgg    900
ctggtaaca                                                            909
```